United States Patent [19]

Fried

[11] Patent Number: 5,175,360
[45] Date of Patent: Dec. 29, 1992

[54] PREPARATION OF ALKOXYALKANOIC ACIDS

[75] Inventor: Herbert E. Fried, Houston, Tex.
[73] Assignee: Shell Oil Company
[21] Appl. No.: 618,205
[22] Filed: Nov. 26, 1990
[51] Int. Cl.$^5$ .................. C07C 51/00; C07C 51/12
[52] U.S. Cl. ................................ 562/538; 562/537
[58] Field of Search ........................... 562/537, 538

[56] References Cited

U.S. PATENT DOCUMENTS

4,620,033 10/1986 Isshiki et al. ..................... 562/519

FOREIGN PATENT DOCUMENTS

5096516 11/1986 Japan .

OTHER PUBLICATIONS

Miyazawa et al., "Oxidation of Benzyl Alcohol with Iron(III) Using Polymers Containing the Nitroxyl Radical Structure as a Mediator," J. Polym. Sci., Polym. Chem. Ed., 23(9), 1985, pp. 2487-2494.
Grigor'ev et al., "Participation of Nitroxyl Radical in the Oxidation of Aldehyde and Alcohol Groups in 3-imidazolin-1-oxyls," Izc. Akad. Nauk. SSSR, Ser. Khim., (1), 1978, pp. 208-210.
Miyazawa et al, "Oxidation of Benzyl Alcohol with Copper(II) Mediated by a Polymeric Oxoaminium Salt," J. Mol. Catal., 49(1), 1988, L31-134
Ganem et al., "Biological Spin Labels as Organic Reagents. Oxidation of Alcohols to Carbonyl Compounds Using Nitroxyls," J. Org. Chem. 40(13), 1975, pp. 1998-2000.
Miyazawa et al., "Oxidation of Benzyl Alcohol by Iron-(iii) Mediated by Nitroxyal Radical," J. Mol. Catal., 31(2), 1985, pp. 217-220.
Anelli et al., "Fast and Selective Oxidation of Primary Alcohols to Aldehydes or to Carboxylic Acids and of Secondary Alcohols to Ketones Mediated by Oxoammonium Salts Under Two-Phase Conditions," J. Org. Chem., 52(12), pp. 2559-2562.
Yamaguchi et al., "Application of Redox System Based on Nitroxides to Organic Synthesis," Pure & Appl. Chem., vol. 62(2), 1990, pp. 217-222.
Inokuchi et al., "A Selective and Efficient Method for Alcohol Oxidations Mediated by N-Oxoammonium Salts in Combination with Sodium Bromite," J. Org. Chem., 55, 1990, pp. 462-466.
Organic Synthesis, vol. 69, p. 212 (1990).

*Primary Examiner*—Arthur C. Prescott
*Assistant Examiner*—V. Garner

[57] ABSTRACT

This invention relates to a process for the preparation of an alkoxyalkanoic acid of the formula $$RO(CH_2CHR'O)_nCH_2CO_2$$

wherein R is an alkyl group of from 1 to about 22 carbon atoms, R' is hydrogen or methyl or mixtures thereof (on the individual molecule) and n is an integer of from 1 to about 12 which comprises reacting the corresponding alkoxyalkanol with a solubilized stable free radical nitroxide having the formula:

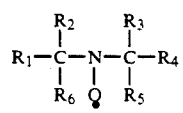

wherein (1) (a) each of $R_1$, $R_2$, $R_3$ and $R_4$ is an alkyl, aryl or heteroatom substituted alkyl group having 1 to about 15 carbon atoms, and (b) $R_5$ and $R_6$ (i) each is an alkyl group having 1 to about 15 carbon atoms provided that when $R_1$-$R_6$ are not all alkyl groups, or a substituted alkyl group having 1 to about 15 carbon atoms wherein the substituent is halogen, cyano, —$CONH_2$, —O-COCH, $OCOC_2H_5$, carbonyl, alkenyl wherein the double bond is not conjugated with the nitroxide moiety, or —COOR wherein R of the —COOR group is alkyl or aryl, or (ii) together form part of a ring that contains 5 carbon atoms and up to two heteroatoms of O or N, or (2) the

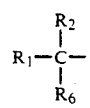

moiety and the

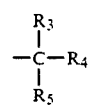

moiety individually are aryl, in the presence of a chlorine-containing oxidant at a temperature in the range of from about −10° C. to about 35° C. and thereafter separating out the alkoxyalkanoic acid.

30 Claims, No Drawings

PREPARATION OF ALKOXYALKANOIC ACIDS

FIELD OF THE INVENTION

This invention relates to a process for the preparation of alkoxyalkanoic acids by the oxidation of the corresponding alkoxyalkanols in the presence of a stable free radical nitroxide.

BACKGROUND OF THE INVENTION

Alkoxyalkanoic acids are useful as anionic detergents. These acids, being composed of only the elements C, H and O, do not pose the environmental problems that other detergents containing heteroatoms such as N, S, and P pose. Commercially, the alkoxyalkanoic acids are prepared in a two-step process of first reacting an alkoxyalkanol with sodium and then reacting the resultant alkoxide with the sodium salt of chloroacetic acid.

It is also known to convert alkoxyalkanols such as methyl carbitol to the corresponding carboxylic acids by oxidizing them with nitric acid. However, not all of the nitric acid can be separated by distillation, and the reaction product contains nitric acid, which is corrosive and therefore undesirable. In addition, cleavage of the ether linkages occurs to a large degree during this process.

Japanese Patent No. 50-96516, issued Jul. 31, 1975, discloses a process for the preparation of carboxylic acid salts by the liquid phase dehydrogenation of alcohols with caustic alkali in the presence of precious metal catalysts, including palladium. This process uses a relatively high temperature, 100° C.-270° C. These high temperatures can degrade the ether linkages especially in the highly ethoxylated alcohols.

It is known to use nitroxyl radicals/oxoammonium salts in the oxidation of primary alcohols to produce aldehydes and acids and secondary alcohols to ketones. *Journal of Organic Chemistry*, vol. 52 (12), pp. 2559-2562; *Pure and Applied Chemistry*, vol. 62(2), 1990, pp. 217-222; *Journal of Organic Chemistry*, vol. 55, 1990, pp. 462-466. The primary products produced in these processes are aldehydes.

It is generally more difficult to oxidize alkoxyalkanols than alkanols as it is difficult to oxidize alkoxyalkanols without splitting the molecular chain at the ether linkage and thereby produce a large proportion of undesired by-product. It is therefore an object of this invention to produce alkoxyalkanoic acids in high yields and with high selectivities from alkoxyalkanols without producing large amounts of other products such as aldehydes.

It is a further object of this invention to provide a process for the preparation of alkoxyalkanoic acids in which highly corrosive, difficult to separate, side-products are not formed.

It has been found that alkoxyalkanoic acids can be produced in high yields and with high selectivities by using catalytic amounts of a stable free radical nitroxide.

SUMMARY OF THE INVENTION

This invention relates to a process for the preparation of an alkoxyalkanoic acid of the formula $$RO(CH_2CHR'O)_nCH_2CO_2H$$

wherein R is an alkyl group of from 1 to about 22 carbon atoms, R' is hydrogen or methyl or mixtures thereof (on the individual molecule) and n is an integer of from 1 to about 12 which comprises reacting the corresponding alkoxyalkanol with a solubilized stable free radical nitroxide having the formula:

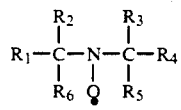

wherein (1) (a) each of $R_1$, $R_2$, $R_3$ and $R_4$ is an alkyl, aryl or heteroatom substituted alkyl group having 1 to about 15 carbon atoms, and (b) $R_5$ and $R_6$ (i) each is an alkyl group having 1 to about 15 carbon atoms provided that $R_1$-$R_6$ are not all alkyl groups, or a substituted alkyl group having 1 to about 15 carbon atoms wherein the substituent is halogen, cyano, —CONH$_2$, —OCOCH, OCOC$_2$H$_5$, carbonyl, alkenyl wherein the double bond is not conjugated with the nitroxide moiety, or —COOR wherein R of the —COOR group is alkyl or aryl, or (ii) together form part of a ring that contains 5 carbon atoms and up to two heteroatoms of O or N, or (2) the

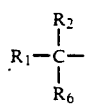

moiety and the

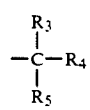

moiety individually are aryl, in the presence of a chlorine-containing oxidant at a temperature in the range of from about 0° C. to about 35° C. and thereafter separating out the alkoxyalkanoic acid.

DESCRIPTION OF THE PREFERRED EMBODIMENTS

The present process converts alkoxyalkanols of the formula $$RO(CH_2CHR'O)_nCH_2CH_2OH \quad (I)$$

wherein R is an alkyl group, preferably 1 to about 22; more preferably about 11 to about 18 carbon atoms, R' is hydrogen or methyl or mixtures thereof (on the individual molecule) and n represents the average number of oxyalkylene groups and is an integer of from 1 to about 12, preferably of from about 2 to about 9, to the corresponding alkoxyalkanoic acids of the formula:

$$RO(CH_2CHR'O)_nCH_2CO_2H \quad (II)$$

by contacting the alkoxyalkanol with a solubilized stable free radical nitroxide in the presence of a chlorine-containing oxidant at a temperature in the range of from about 0° C. to about 35° C. The R group in the above formula I can be substituted with any substituent which does not interfere with the oxidation of the hydroxy group. Such substituents include —OR", —CH$_3$, —COOH, CONH$_2$ and COOR" wherein R" is an alkyl or aryl group. The process of the instant invention is particularly suited to detergent range ethoxylated, or propoxylated alcohols with alkyl chains (R) of about 8 to about 20, preferably of about 11 to about 18 carbon atoms. The R' groups on an individual molecule can be hydrogen, methyl or mixtures thereof. For example, straight ethoxylated, straight propoxylated and mixed ethoxylatedpropoxylated detergent alcohols are commercially available. The number of such alkoxylate groups, (CH$_2$CHR'O), range from 1 to about 20. Commercially, detergent range ethoxylate alcohols are available with an average of 3, 7, 9 and 12 ethoxylate units per molecule. Others can be readily prepared. In a preferred embodiment, the starting alkoxyalkanol is ethoxylated alcohol which has had the unreacted alcohols and lower ethoethoxylates topped off in order to give an ethoxylate having about four ethylene oxide units per molecule.

The term "stable free radical nitroxide" as used herein shall mean a free radical nitroxide that can be prepared by conventional chemical methods and will exist long enough to be used in a subsequent chemical reaction or examined in a static system by normal methods of spectroscopy. Generally, the stable free radical nitroxides of the present invention have a half life of at least one year. The term "stable free radical" shall also be understood to include the precursor to a stable free radical from which the stable free radical may be produced in situ.

The stable free radical nitroxides, as used in the present process, are precursors to catalysts, i.e., oxoammonium salts, active for the oxidation of alkoxyalkanols to the corresponding acids. These catalysts are generated in situ by the oxidation of a stable free radical nitroxide to an oxoammonium salt with a chlorine-containing oxidant. The stable free radical nitroxide can be obtained by the oxidation of secondary amines or hydroxylamines.

The stable free radical nitroxides which are suitable for use in the instant invention have the formula:

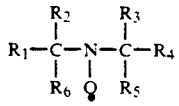
(III)

wherein each of R$_1$, R$_2$, R$_3$ and R$_4$ is an alkyl, aryl or heteroatom substituted alkyl groups and no hydrogen is bound to the remaining valences on the carbon atoms bound to the nitrogen. As used herein, the term "alkyl" is meant to include cycloalkyl. The alkyl (or heteroatom substituted) groups R$_1$-R$_4$ may be the same or different, and preferably contain 1 to 15 carbon atoms. Preferably, R$_1$-R$_4$ are methyl, ethyl, or propyl groups. In addition to hydrogen, the heteroatom substituents may include, halogen, oxygen, nitrogen and the like.

The remaining valences (R$_5$ and R$_6$) in formula III above may be satisfied by any atom or group except hydrogen which can bond covalently to carbon, although some groups may reduce the stabilizing power of the nitroxide and are undesirable. When R$_1$, R$_2$, R$_3$ and R$_4$ are each alkyl groups, however, at least one of R$_5$ and R$_6$ must be an aryl group. Preferably, R$_5$ and R$_6$ are substituted alkyl groups having 1 to about 15 carbon atoms wherein the substituent is selected from halogen, cyano, —COOR, wherein R is alkyl or aryl, —CONH$_2$, —OCOC$_2$H$_5$, carbonyl, or alkenyl where the double bond is not conjugated with the nitroxide moiety, or alkyl groups of 1 to about 15 carbon atoms. R$_5$ and R$_6$ may also form a ring of carbon atoms and up to two heteroatoms, such as O or N, by R$_5$ and R$_6$ together. Examples of suitable compounds having the structure above and in which R$_5$ and R$_6$ form part of the ring are piperidinyl-1-oxyls and pyrrolidin-1-oxyls. Particular examples wherein R$_5$ and R$_6$ above form part of a ring are 2,2,6,6-tetramethyl-piperidine-1-oxyl, 4-hydroxy-2,2,6,6-tetramethyl-piperidine-1-oxyl and 4-oxo-2,2,6,6-tetramethyl-piperidine-1-oxyl.

The

and the

moieties in formula III above can individially be aryl, i.e.,

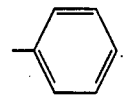

Examples of suitable compounds having the structure above in which the

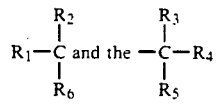

moieties are individually aryl are diphenylamine, phenyl tertiary butylamine 3-methyldiphenylamines, 2-chlorophenylamine and the like. These compounds may be substituted with any substituents which do not interfere with the reaction.

The preferred nitroxides for use in the instant invention are those wherein R$_5$ and R$_6$ form a ring structure with the nitrogen, and preferably a six membered ring. Preferably, the nitroxide is selected from the group consisting of 2,2,6,6-tetramethyl-piperidine-1-oxyl, 4-hydroxy-2,2,6,6-tetramethyl-piperidine-1-oxyl, 4-oxo-2,2,6,6-tetramethyl-piperidine-1-oxyl, 2,2,6,6-tetramethyl-piperidine-1-oxyl-4-sulfate, 4-oxo-2,2,6,6-tetramethyl-piperidine, 4-hydroxy-2,2,6,6-tetramethyl-piperidine and mixtures thereof, with 2,2,6,6-tetramethyl-piperidine-1-oxyl, 2,2,6,6-tetramethyl-piperidine-1-oxyl-4-sulfate, and 4-hydroxy-2,2,6,6-tetramethyl-piperidine-1-oxyl being particularly preferred.

In one embodiment, the stable free radical nitroxide can be supported on a polystyrene resin such as, for example, by reacting 4-hydroxy-2,2,6,6-tetramethyl-piperidine-1-oxyl with chloromethylated polystyrene to form a covalently linked resin. The use of a resin-supported nitroxide is advantageous in that by simple filtration, the catalyst can be easily separated from the product.

The chlorine-containing oxidants suitable for use in the instant invention are chlorine-containing compounds which are capable of oxidizing the stable free radical nitroxide to the oxoammonium salt. Suitable chlorine-containing oxidants include chlorine, hypochlorite and N-chloro compounds, with chlorine and hypochlorite being preferred. Suitable hypochlorite oxidants include sodium hypochlorite, which is typically used in an aqueous solution having a concentration of up to about 10%, preferably from about 2.5% to about 5%. When chlorine is used as the oxidant, chlorine is suitably bubbled into the reaction solution.

The amounts and concentrations of the reactants utilizied in the process of the instant invention can vary within wide ranges. The amount of stable free radical nitroxide utilized depends on the manner in which the reagents are contacted. The chlorine-containing oxidant is typically added last, i.e. the chlorine-containing oxidant is added slowly to a reaction mixture containing alkoxyalkanol, solvent and nitroxide. When this procedure is used, the amount of nitroxide is typically in the range of from about 500 parts per million to about 30,000 parts per million, preferably from about 1,000 parts per million to about 10,000 parts per million, and more preferably from about 1,000 parts per million to about 4,000 parts per million, basis the weight of the starting alkoxyalkanol. Alternatively, the chlorine containing oxidant may be added prior to the addition of the nitroxide, in which case the amount of nitroxide utilized will typically be in the range of from about 100 parts per million to about 3,000 parts per million. Generally, the amount of chlorine-containing oxidant utilized when the oxidant is sodium hypochlorite will be in the range of from about 2.0 equivalents to about 2.5 equivalents, preferably from about 2.3 equivalents to about 2.5 equivalents, basis the weight of the starting alkoxyalkanol.

The reaction in the instant invention is carried out utilizing a solubilized stable free radical nitroxide. The solvent is typically a nonaqueous solvent which is to a large extent immiscible in water and in which the alkoxyalkanol is readily soluble. Solvents which are most suitable are those having dielectric constants greater than about 2. The solvent may be added to the reaction mixture or, alternatively, the nitroxide may be dissolved in the solvent prior to addition of the nitroxide to the reaction medium. The solvent is typically selected from the group consisting of ethyl acetate, dichloromethane, acetonitrile, toluene, chlorobenzene, xylene, carbon tetrachloride, chloroform, tetrachloroethylene, diethyl ether, methyl-tert-butyl ether and mixtures thereof, with ethyl acetate and dichloromethane being preferred. The amount of solvent utilized in the process is generally from about 10:1 to about 0.5:1, preferably from about 7:1 to about 3:1, and more preferably from about 4:1 to about 3:1, basis the weight of the starting alkoxyalkanol.

The reaction is suitably begun in a neutral to slightly basic medium. If the reaction is conducted in a medium which is initially too basic, the start of the oxidation reaction will be extremely slow and lead to longer reaction times. If the reaction is conducted in a medium which is buffered and is too basic, the oxidation reaction will be extremely slow and lead to low conversion of the alkoxyalkanol to the corresponding acid. On the other hand, if the reaction medium is too acidic, the reaction may result in higher amounts of esters than is desirable. Thus, in a preferred embodiment, an acid is added to the reaction mixture either at the beginning of the reaction or after partial completion of the reaction to adjust the pH to a value of about 8-9. Suitable acids include hydrochloric acid, sulfuric acid, phosphoric acid and the like. Alternatively, the pH of the reaction mixture may be adjusted by recycling alkoxyalkanoic acid produced according to the invention. The concentration of the acid will typically be in the range of from about 1% to about 20%, preferably in the range of from about 1% to about 10%. The pH of the reaction steadily decreases as the reaction proceeds and acids are formed. The final pH of the reaction mixture is generally in the range of from about 0 to about 5. The acid product may be produced at least in part in the form of its alkali metal salt and it is to be understood that the term "acid" as used in the specification and the appended claims is intended to include the salt form as well as the free acid form.

The process of the present invention is typically conducted under mild conditions, with good results being obtained using a temperature in the range of from about $-10°$ C. to about $35°$ C., preferably about $0°$ C. to about $30°$ C., more preferably about $10°$ C. to about $25°$ C., and most preferably about $20°$ C. Reaction pressures are not critical and atmospheric pressure is typically used.

The process of the instant invention can be carried out either batchwise or continuously, using a stirrer equipped reactor or other well known contacting technique to achieve adequate mixing. Preferred reaction conditions, e.g., temperature, pressure, flow rates, etc., vary somewhat depending on the specific nitroxide utilized and on the concentration of the nitroxide.

The process of the instant invention can be carried out in a variety of ways. For example, one equivalent of alkoxyalkanol, 1,000–4,000 parts per million of the nitroxide and solvent may be added to the reaction vessel, followed by the addition of two equivalents of aqueous sodium hypochlorite. Alternatively, one equivalent of alkoxyalkanol and two equivalents of aqueous sodium hypochlorite and solvent may be added to the reaction vessel and allowed to reach equilibrium, followed by the dropwise or immediate addition of 100–3,000 parts per million of the nitroxide which has been dissolved in a minimum amount of solvent. In a preferred embodiment, the reaction is carried out by adding the alkoxyalkanol, nitroxide and solvent together and then adding the hypochlorite to the mixture. Following the reaction, the product may be separated from the reaction mixture using conventional procedures such as extraction using a suitable extraction solvent such as, for example, ethyl acetate; evaporation wherein the solvent is stripped from the reaction mixture by using heat or vacuum. Phase separation of the acidified solution takes place at $100°$ C. with water. The reaction product can be purified by a number of conventional means such as high temperature water washing or catalytic hydrogenation.

Depending upon process conditions and the nitroxide used, the yields of alkoxyalkanoic acid obtained by this invention can be greater than about 99% of starting material being converted. The products produced by the instant process can be used in a variety of detergent applications. For example, light duty dishwashing liquids, shampoos and heavy duty laundry liquids or powders.

The ranges and limitations provided in the instant specification and claims are those which are believed to particularly point out and distinctly claim the present invention. It is, however, understood that other ranges and limitations which perform substantially the same function in the same or substantially the same manner to obtain the same or substantially the same result are intended to be within the scope of the instant invention as defined by the instant specification and claims.

The process of this invention will be further described by the following embodiments which are provided for illustration and are not to be construed as limiting the invention.

ILLUSTRATIVE EMBODIMENTS

In the following examples, the starting alkoxyalkanol was a NEODOL ® Ethoxylate 23-3T alcohol which was prepared by ethoxylating a mixture of $C_{12}$ and $C_{13}$ substantially straight chain alcohols ($C_{12}:C_{13} \sim 40:60$) to an ethoxylate alcohol having about 3 ethylene oxide units per molecule and then topping off the unreacted alcohols and lower ethoxylates so that the final product has about three ethylene oxide units per molecule.

EXAMPLE 1

Thirty-one grams of NEODOL ® Ethoxylate 23-3T, 0.5 grams of 2,2,6,6-tetramethyl-piperidine-1-oxyl and 125 milliliters of dichloromethane were charged to a 1 liter round bottomed flask. To this mixture was added 282 grams of 5.25% sodium hypochlorite in which the pH was adjusted to 8.6 by the addition of 2.6 grams of 25% sulfuric acid. The reaction temperature was held at 20° C. over a six hour period. The results are presented in Table I.

EXAMPLE 2

31.4 grams of NEODOL ® Ethoxylate 23-3T, 0.125 grams of 2,2,6,6-tetramethyl-piperidine-1-oxyl and 125 milliliters of dichloromethane were charged to a 1 liter round bottomed flask. To this mixture was added 282 grams of 5.25% sodium hypochlorite in which the pH was adjusted to 8.6 by the addition of 2.6 grams of 25% sulfuric acid. The reaction temperature was held at 20° C. over a six hour period. The results are presented in Table I.

EXAMPLE 3

31.7 grams of NEODOL ® Ethoxylate 23-3T, 0.125 grams of 2,2,6,6-tetramethyl-piperidine-1-oxyl, 100 milliliters of ethyl acetate, and 5 grams of alkoxyalkanoic acid were charged to a 1 liter round bottomed flask. To this mixture was added 282 grams of 5.25% sodium hypochlorite. The reaction temperature was held at 20° C. over a four hour period. The results are presented in Table I.

COMPARATIVE EXAMPLE A

Comparative A was carried out in a manner similar to Example 1 except that di-tert-butyl nitroxide was used as the nitroxide. The results are presented in Table I.

COMPARATIVE EXAMPLE B

Comparative B was carried out in a manner similar to Example 1 except that no nitroxide was used. The results are presented in Table I.

TABLE 1

Oxidation of Alkoxyalkanols to Alkoxyalkanoic Acid

| | % Conversion | % Sel. AEC | % Sel. Ester | % Sel. Formates | % Sel. Fatty Acids |
|---|---|---|---|---|---|
| Example 1 | >99 | 90 | 5.1 | 3.2 | 1.2 |
| Example 2 | 97 | 93 | 7 | <1 | <1 |
| Example 3 | 99 | 89 | 5.1 | 3.5 | 2.4 |
| Comparative Example A | 43 | <1 | 97 | 1 | 2 |
| Comparative Example B | 13 | 50 | 38 | 6 | 6 |

What is claimed is:

1. A process for the preparation of an alkoxyalkanoic acid of the formula $$RO(CH_2CHR'O)_nCH_2CO_2H$$

wherein R is an alkyl group of from 1 to about 22 carbon atoms, R' is hydrogen or methyl or mixtures thereof (on the individual molecule) and n is an integer of from 1 to about 12 which comprises reacting the corresponding alkoxyalkanol with a solubilized stable free radical nitroxide having the formula:

wherein (1) (a) each of $R_1$, $R_2$, $R_3$ and $R_4$ is an alkyl or aryl group having 1 to about 15 carbon atoms, and (b) $R_5$ and $R_6$ (i) each is an alkyl group having 1 to about 15 carbon atoms provided that $R_1$-$R_6$ are not all alkyl groups, or a substituted alkyl group having 1 to about 15 carbon atoms wherein the substituent is halogen, cyano, —$CONH_2$, —$OCOCH$, $OCOC_2H_5$, carbonyl, alkenyl wherein the double bond is not conjugated with the nitroxide moiety, or —COOR wherein R of the —COOR group is alkyl or aryl, or (ii) together form part of a ring that contains 5 carbon atoms and up to two heteroatoms of O or N, or (2) the

moiety and the

moiety individually are aryl, in the presence of a chlorine-containing oxidant selected from chlorine and hypochlorite at a temperature in the range of from about −10° C. to about 35° C. and thereafter separating out the alkoxyalkanoic acid.

2. The process of claim 1 wherein the solubilized stable free radical nitroxide is selected from the group consisting of 2,2,6,6-tetramethyl-piperidine-1-oxyl, 4-hydroxy-2,2,6,6-tetramethyl-piperidine-1-oxyl, 4-oxo-2,2,6,6-tetramethyl-piperidine-1-oxyl, 2,2,6,6-tetramethyl-piperidine-1-oxyl-4-sulfate, 4-oxo-2,2,6,6-tetramethyl-piperidine, 4-hydroxy-2,2,6,6-tetramethyl-piperidine and mixtures thereof.

3. The process of claim 1 wherein the solubilized stable free radical nitroxide is selected from the group consisting of 2,2,6,6-tetramethyl-piperidine-1-oxyl, 2,2,6,6-tetramethyl-piperidine-1-oxyl-4-sulfate, 4-hydroxy-2,2,6,6-tetramethyl-piperidine-1-oxyl and mixtures thereof.

4. The process of claim 1 wherein the stable free radical nitroxide is dissolved in a solvent selected from the group consisting of ethyl acetate, dichloromethane, acetonitrile, toluene, chlorobenzene, xylene, carbon tetrachloride, chloroform, tetrachloroethylene, diethyl ether, methyl-tert-butyl ether and mixtures thereof.

5. The process of claim 4 wherein the stable free radical nitroxide is dissolved in a solvent selected from the group consisting of dichloromethane, ethyl acetate and mixtures thereof.

6. The process of claims 1 or 4 wherein said alkoxyalkanol is contacted with said solubilized stable free radical nitroxide, followed by the addition thereto of said chlorine-containing oxidant.

7. The process of claim 6 wherein the amount of solubilized stable free radical nitroxide is in the range of from about 500 parts per million to about 30,000 parts per million, basis the weight of the alkoxyalkanol.

8. The process of claim 6 wherein the amount of solubilized stable free radical nitroxide is in the range of from about 1,000 parts per million to about 10,000 parts per million, basis the weight of the alkoxyalkanol.

9. The process of claim 6 wherein the amount of solubilized stable free radical nitroxide is in the range of from about 1,000 parts per million to about 4,000 parts per million, basis the weight of the alkoxyalkanol.

10. The process of claims 1 or 4 wherein said alkoxyalkanol is contacted with said chlorine-containing oxidant, followed by the addition thereto of said stable free radical nitroxide.

11. The process of claim 10 wherein the amount of solubilized stable free radical nitroxide is in the range of from about 100 parts per million to about 3,000 parts per million, basis the weight of the alkoxyalkanol.

12. The process of claim 1 wherein said chlorine-containing oxidant is aqueous sodium hypochlorite having a concentration of up to about 10%.

13. The process of claim 1 wherein said chlorine-containing oxidant is chlorine.

14. The process of claim 1 wherein said process is carried out at a temperature in the range of from about 0° C. to about 30° C. and at atmospheric pressure.

15. The process of claim 14 wherein said process is carried out at a temperature in the range of from about 10° C. to about 25° C. and at atmospheric pressure.

16. A process for the preparation of an alkoxyalkanoic acid of the formula

RO(CH$_2$CHR'O)$_n$CH$_2$CO$_2$H wherein R is an alkyl group of from 1 to about 22 carbon atoms, R' is hydrogen or methyl or mixtures thereof (on the individual molecule) and n is an integer of from 1 to about 12 which comprises reacting the corresponding alkoxyalkanol with a solubilized stable free radical nitroxide having the formula:

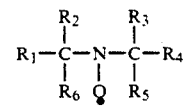

wherein each of $R_1$, $R_2$, $R_3$ and $R_4$ is an alkyl or aryl group having 1 to about 15 carbon atoms, and $R_5$ and $R_6$ together form part of a ring that contains 5 carbon atoms and up to two heteroatoms of O or N, in the presence of a chlorine-containing oxidant at a temperature in the range of from about −10° C. to about 35° C. and thereafter separating out the alkoxyalkanoic acid.

17. The process of claim 16 wherein the solubilized stable free radical nitroxide is selected from the group consisting of 2,2,6,6-tetramethyl-piperidine-1-oxyl, 4-hydroxy-2,2,6,6-tetramethyl-piperidine-1-oxyl, 4-oxo-2,2,6,6-tetramethyl-piperidine-1-oxyl, 2,2,6,6-tetramethyl-piperidine-1-oxyl-4-sulfate, 4-oxo-2,2,6,6-tetramethyl-piperidine, 4-hydroxy-2,2,6,6-tetramethyl-piperidine and mixtures thereof.

18. The process of claim 16 wherein the solubilized stable free radical nitroxide is selected from the group consisting of 2,2,6,6-tetramethyl-piperidine-1-oxyl, 2,2,6,6-tetramethyl-piperidine-1-oxyl-4-sulfate, 4-hydroxy-2,2,6,6-tetramethyl-piperidine-1-oxyl and mixtures thereof.

19. The process of claim 16 wherein the stable free radical nitroxide is dissolved in a solvent selected from the group consisting of ethyl acetate, dichloromethane, acetonitrile, toluene, chlorobenzene, xylene, carbon tetrachloride, chloroform, tetrachloroethylene, diethyl ether, methyl-tert-butyl ether and mixtures thereof.

20. The process of claim 19 wherein the stable free radical nitroxide is dissolved in a solvent selected from the group consisting of dichloromethane, ethyl acetate and mixtures thereof.

21. The process of claims 16 or 19 wherein said alkoxyalkanol is contacted with said solubilized stable free radical nitroxide, followed by the addition thereto of said chlorine-containing oxidant.

22. The process of claim 21 wherein the amount of solubilized stable free radical nitroxide is in the range of from about 500 parts per million to about 30,000 parts per million, basis the weight of the alkoxyalkanol.

23. The process of claim 21 wherein the amount of solubilized stable free radical nitroxide is in the range of from about 1,000 parts per million to about 10,000 parts per million, basis the weight of the alkoxyalkanol.

24. The process of claim 21 wherein the amount of solubilized stable free radical nitroxide is in the range of from about 1,000 parts per million to about 4,000 parts per million, basis the weight of the alkoxyalkanol.

25. The process of claims 16 or 19 wherein said alkoxyalkanol is contacted with said chlorine-containing oxidant, followed by the addition thereto of said stable free radical nitroxide.

26. The process of claim 25 wherein the amount of solubilized stable free radical nitroxide is in the range of from about 100 parts per million to about 3,000 parts per million, basis the weight of the alkoxyalkanol.

27. The process of claim 16 wherein said chlorine-containing oxidant is aqueous sodium hypochlorite having a concentration of up to about 10%.

28. The process of claim 16 wherein said chlorine-containing oxidant is chlorine.

29. The process of claim 16 wherein said process is carried out at a temperature in the range of from about 0° C. to about 30° C. and at atmospheric pressure.

30. The process of claim 29 wherein said process is carried out at a temperature in the range of from about 10° C. to about 25° C. and at atmospheric pressure.

* * * * *